(12) United States Patent
Pellicciari et al.

(10) Patent No.: US 7,858,608 B2
(45) Date of Patent: Dec. 28, 2010

(54) BILE ACID DERIVATIVES AS FXR LIGANDS FOR THE PREVENTION OR TREATMENT OF FXR-MEDIATED DISEASES OR CONDITIONS

(75) Inventors: Roberto Pellicciari, Perugia (IT); Stefano Fiorucci, Perugia (IT); Mark Pruzanski, New York, NY (US)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 12/435,063

(22) Filed: May 4, 2009

(65) Prior Publication Data
US 2010/0063018 A1    Mar. 11, 2010

Related U.S. Application Data

(63) Continuation of application No. 12/279,320, filed as application No. PCT/US2007/003678 on Feb. 14, 2007, now abandoned.

(60) Provisional application No. 60/772,900, filed on Feb. 14, 2006.

(51) Int. Cl.
*A61K 31/575* (2006.01)
*C07J 41/00* (2006.01)

(52) U.S. Cl. ...................... 514/182; 552/554
(58) Field of Classification Search .......... 514/182; 552/554
See application file for complete search history.

(56) References Cited

PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26).*
* cited by examiner

*Primary Examiner*—Barbara P Badio
(74) *Attorney, Agent, or Firm*—Ivor R. Elrifi, Esq.; Jennifer Loebach, Esq.; Mintz, Levin, Cohn, Ferris, Glovsky and Popeo, P.C.

(57) ABSTRACT

The present invention relates to compounds of formula (I)

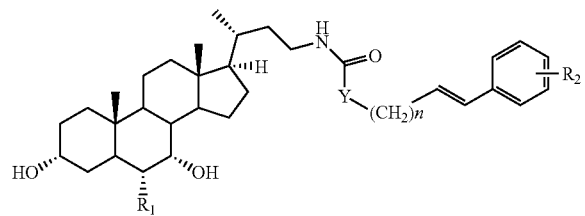

wherein:
$R_1$ is hydrogen or an alkyl group;
$R_2$ is hydrogen or a halogen, nitro, alkyloxy, amino or carboxy group;
Y is $CH_2$, oxygen or sulfur;
n is an integer from 1 to 4, and pharmaceutically acceptable salts, solvates or amino acid conjugates thereof for the treatment of FXR-mediated diseases or conditions.

5 Claims, 1 Drawing Sheet

BILE ACID DERIVATIVES AS FXR LIGANDS FOR THE PREVENTION OR TREATMENT OF FXR-MEDIATED DISEASES OR CONDITIONS

This application is a continuation application and claims priority under 35 U.S.C. 120 to U.S. non-provisional application Ser. No. 12/279,320, now abandoned, which is a U.S. national stage application, filed under 35 U.S.C. 371, of International Application PCT/US 07/003678, filed Feb. 14, 2007, which claims priority under 35 U.S.C. 119(e) to U.S. provisional application Ser. No. 60/772,900, filed Feb. 14, 2006.

FIELD OF THE INVENTION

The present invention relates to Farnesoid X receptors (FXR) modulators which can be used for the treatment of cholestatic disorders, in particular to bile acids derivatives wherein the $C_{24}$ carboxy group is transformed into an amido, carbamido or thiocarbamido group.

BACKGROUND OF THE INVENTION

Farnesoid X Receptor (FXR) is an orphan nuclear receptor initially identified from a rat liver cDNA library (B M. Forman, et al., *Cell* 81:687-693 (1995)) that is most closely related to the insect ecdysone receptor. FXR is a member of the nuclear receptor family of ligand-activated transcription factors that includes receptors for the steroid, retinoid, and thyroid hormones (D J. Mangelsdorf, et al., *Cell* 83:841-850 (1995)). Northern and in situ analysis show that. FXR is most abundantly expressed in the liver, intestine, kidney, and adrenal (B M. Forman, et al., *Cell* 81:687-693 (1995) and W. Seol, et al., *Mol. Endocrinnol.* 9:72-85 (1995)). FXR binds to DNA as a heterodimer with the 9-cis retinoic acid receptor (RXR). The FXR/RXR heterodimer preferentially binds to response elements composed of two nuclear receptor half sites of the consensus AG(G/T)TCA organized as an inverted repeat and separated by a single nucleotide (IR-1 motif) (B M. Forman, et al., *Cell* 81:687-693 (1995)). An early report showed that rat FXR is activated by micromolar concentrations of farnesoids such as farnesol and juvenile hormone (B M. Forman, et al., *Cell* 81:687-693 (1995)). However, these compounds failed to activate the mouse and human FXR, leaving the nature of the endogenous FXR ligand in doubt. Several naturally-occurring bile acids bind to and activate FXR at physiological concentrations (PCT WO 00/37077, published 29 Jun. 2000)). As discussed therein, the bile acids that serve as FXR ligands include chenodeoxycholic acid (CDCA), deoxycholic acid (DCA), lithocholic acid (LCA), and the taurine and glycine conjugates of these bile acids.

Bile acids are cholesterol metabolites that are formed in the liver and secreted into the duodenum of the intestine, where they have important roles in the solubilization and absorption of dietary lipids and vitamins. Most bile acids (~95%) are subsequently reabsorbed in the ileum and returned to the liver via the enterohepatic circulatory system. The conversion of cholesterol to bile acids in the liver is under feedback regulation: bile acids down-regulate the transcription of cytochrome P450 7a (CYP7a), which encodes the enzyme that catalyzes the rate limiting step in bile acid biosynthesis. There are data to suggest that FXR is involved in the repression of CYP7a expression by bile acids, although the precise mechanism remains unclear (D W. Russell, *Cell* 97:539-542 (1999)). In the ileum, bile acids induce the expression of the intestinal bile acid binding protein (IBABP), a cytoplasmic protein which binds bile acids with high affinity and may be involved in their cellular uptake and trafficking. Two groups have now demonstrated that bile acids mediate their effects on IBABP expression through activation of FXR, which binds to an IR-1 type response element that is conserved in the human, rat, and mouse IBABP gene promoters (14; 17). Thus FXR is involved in both the stimulation (IBABP) and the repression (CYP7a) of target genes involved in bile acid and cholesterol homeostasis.

EP 1392714 discloses 3α,7β-dihydroxy-6α-ethyl-5β-cholan-24-oic acid (hereinafter also referred to as 6-ethyl-chenodeoxycholic acid, 6-EDCA), solvates and amino acids conjugates thereof as FXR agonists, which can be used in the preparation of medicaments for the prevention or treatment of FXR-mediated diseases or conditions.

EP 1568796 discloses 6-ethyl-ursodeoxycholic acid (6-EUDCA) derivatives as FXR agonists and their use in the prevention or treatment of FXR-mediated diseases or conditions.

SUMMARY OF THE INVENTION

The present invention provides compounds of general formula (I):

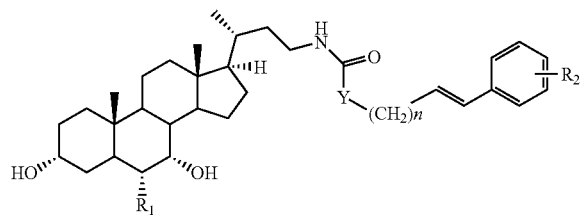

(I)

wherein $R_1$ is hydrogen or an alkyl group; $R_2$ is hydrogen or a halogen, nitro, alkyloxy, amino or carboxy group; Y is a methylene group, oxygen or sulfur; and n is an integer from 1 to 4, and pharmaceutically acceptable salts, solvates or amino acid conjugates thereof.

In another aspect, the present invention provides a compound of formula (I), wherein $R_1$ and $R_2$ are hydrogen, Y is oxygen, and n is 1 (formula Ia).

In another aspect, the present invention provides a method for the prevention or treatment of an FXR-mediated disease or condition in a mammal comprising administering to a mammal suffering from a FXR-mediated disease or condition a therapeutically effective amount of a compound of formula (I) or (Ia). The present invention also provides the use of a compound of formula (I) or (Ia) for the preparation of a medicament for the prevention or treatment of a FXR-mediated disease or condition. In certain embodiments, the FXR-mediated disease or condition is a liver disease or condition, gastrointestinal disease or condition, renal disease or condition, cardiovascular disease or condition, or metabolic disease or condition. In certain embodiments, the liver disease or condition is primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, or $α_1$-antitrypsin deficiency. In certain embodiments, the gastrointestinal disease or condition is inflammatory bowel disease (IBD) (including Crohn's disease and ulcerative colitis), irritable bowel syndrome (IBS), bacterial overgrowth, malabsorption, post-radiation colitis, or microscopic colitis. In certain embodiments, the renal disease or condition is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease. In certain embodiments, the cardiovascular disease or condition is atherosclerosis, arteriosclerosis, dyslipidemia, hypercholesterolemia, or hypertriglyceridemia. In certain embodiments, the metabolic disease or condition is insulin resistance, diabetes, or obesity.

In another aspect, the present invention provides a pharmaceutical formulation comprising a compound of formula (I) or (Ia) and a pharmaceutically acceptable carrier or diluent. The present invention also provides pharmaceutical compositions containing a compound of formula (I) or (Ia) in admixture with pharmaceutically acceptable carriers and/or diluents.

In another aspect, the present invention provides a radiolabeled compound of formula (I) or (Ia). In another embodiment, a compound of formula (I) or (Ia) is tritiated.

DETAILED DESCRIPTION OF THE INVENTION

Figure 1:
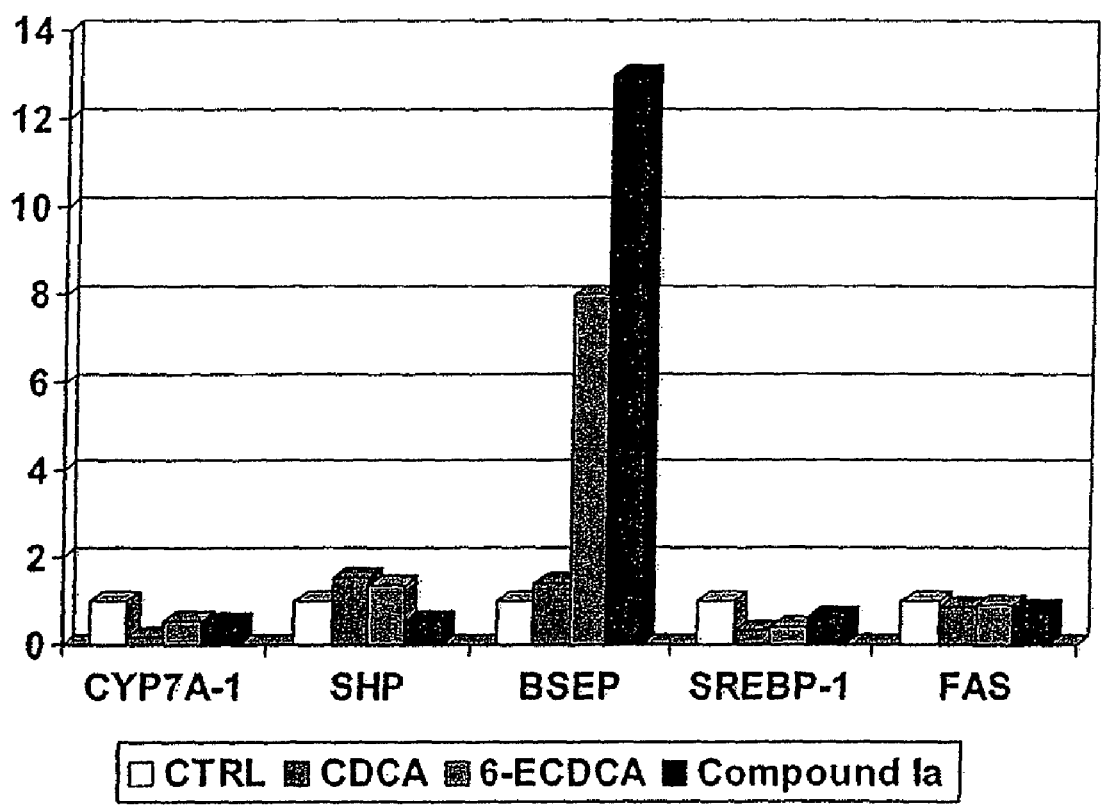
FIG. 1 shows the effect of compound Ia on selective genes. Human hepatocyte cell line HepG2 was used for these studies. Cells were exposed to 10 μM of CDCA, 6-ECDCA and compound (Ia) for 18 hours and the expression of CYP7A1, SHP, BSEP, SREPB-1C and FAS was measured by qRT-PCR. The FIGURE reports the results reported of one experiment out of 4 showing the same pattern.

The present invention relates to compounds of general formula (I):

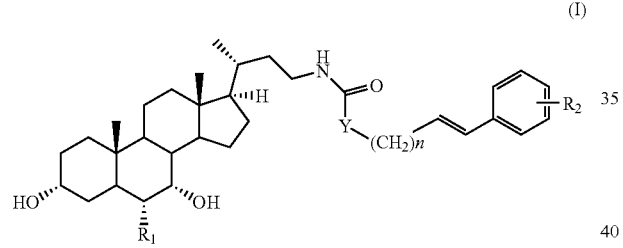

wherein:
$R_1$ is hydrogen or an alkyl group;
$R_2$ is hydrogen or a halogen, nitro, alkyloxy, amino or carboxy group;
Y is a methylene group, oxygen or sulfur;
n is an integer from 1 to 4, and pharmaceutically acceptable salts, solvates or amino acid conjugates thereof.

For the purposes of the present application, "alkyl" means a straight or branched alkyl chain containing 1 to 6 carbon atoms and "halogen" means a halogen atom selected from fluorine, chlorine, bromine and iodine.

Suitable pharmaceutically acceptable salts according to the present invention will be readily determined by one skilled in the art and will include, for example, basic salts such as metallic salts made from aluminum, calcium, lithium, magnesium, potassium, sodium, and zinc or organic salts made from N,N'-dibenzylethylenediamine, chlorprocaine, choline, diethanolamine, ethylendiamine, meglumine (N-methylglucamine), and procaine. Such salts of the compounds of formula (I) may be prepared using conventional techniques, from a compound of formula (I) by reacting, for example, the appropriate base with a compound of formula (I).

When used in medicine, the salts of a compound of formula (I) should be pharmaceutically acceptable, but pharmaceutically unacceptable salts may conveniently be used to prepare the corresponding free base or pharmaceutically acceptable salts thereof.

As used herein, the term "solvate" is a crystal form containing a compound of formula (I) or a pharmaceutically acceptable salt thereof and either a stoichiometric or a non-stoichiometric amount of a solvent. Solvents, by way of example, include water, methanol, ethanol, or acetic acid. Hereinafter, reference to a compound of formula (I) is to any physical form of that compound, unless a particular form, salt or solvate thereof is specified.

As used herein, the term "amino acid conjugates" refers to conjugates of a compound of formula (I) with any suitable amino acid. Preferably, such suitable amino acid conjugates of a compound of formula (I) will have the added advantage of enhanced integrity in bile or intestinal fluids. Suitable amino acids include but are not limited to glycine and taurine.

The compounds of the invention can be prepared by methods well known in the fields of organic synthesis.

Compounds of formula (I) wherein Y is a methylene group can be prepared by transforming the $C_{24}$ carboxy group of chenodeoxycholic acid (II) into an amino group and then reacting this amino derivative with an activated carboxylic acid of formula (III)

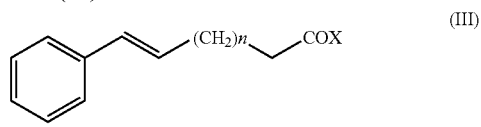

wherein X is a carboxy-activating group.

Compounds of formula (I) wherein Y is oxygen or sulfur can be prepared by transforming the $C_{24}$ carboxy group of chenodeoxycholic acid (II) into an isocyanate group and then reacting the isocyanate derivative with a suitable alcohol or thiol of formula (IV)

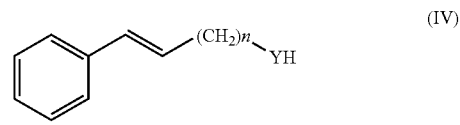

wherein Y is oxygen or sulfur.

This synthetic approach is briefly resumed herein below and illustrated in scheme 1 for the compound of formula (Ia), wherein $R_1$ and $R_2$ are hydrogen, Y is oxygen and n is 1, which is the most preferred embodiment of the invention. 3α,7α-diformyl-chenodeoxycholic acid (CDCA) (V), obtained as reported in Goto, J. et al. *Chem. Pharm. Bull.* 1979, 27, 1402-1411, is converted into the corresponding acyl azide, via an acyl chloride intermediate by treatment first with oxalyl chloride and then with aqueous sodium azide. The crude acyl azide mixture is then converted to the corresponding isocyanate (VI) by Curtius rearrangement. Intermediate (VI) is then reacted with cinnamyl alcohol (or another suitable alcohol IV) to obtain the 3α,7α-diprotected-CDCA carbamate analogue, which, after basic hydrolysis, gives the desired compound (Ia).

Scheme 1

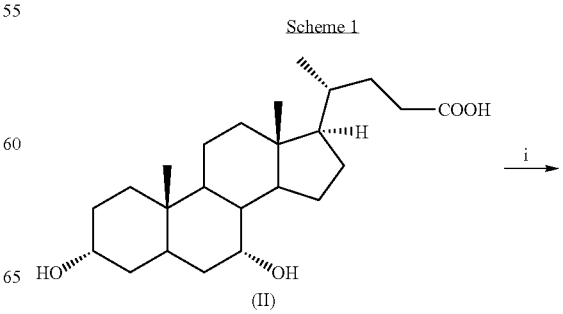

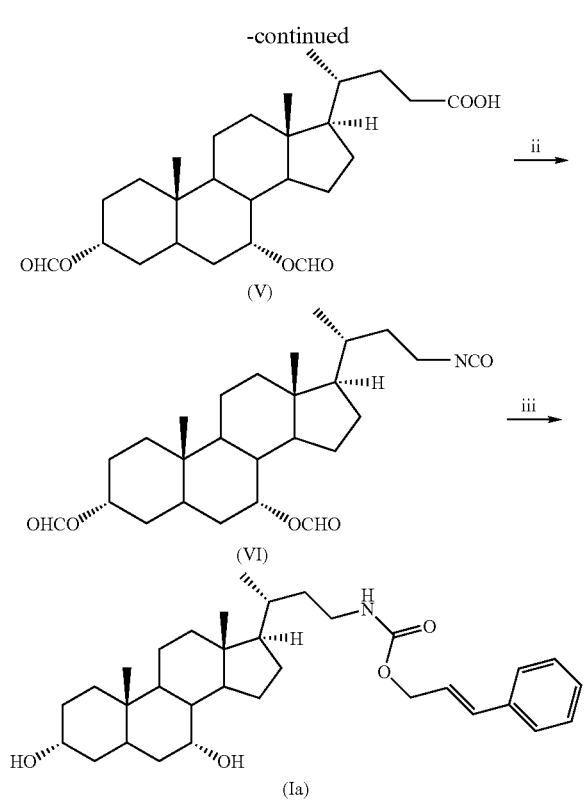

As explained in greater detail in the experimental section, compound (Ia) was tested in cell-free assays and on a human hepatocyte cell line. This (Ia) proved approximately 20-fold more potent than chenodeoxycholic acid (CDCA) in activating FXR and caused 13-fold induction of a FXR-regulated gene and bile acid transporter, BSEP (bile salt export pump). In contrast to natural FXR ligands such as CDCA, compound (Ia) does not induce the small heterodimeric partner (SHP, an atypical nuclear receptor that lacks a DNA-binding domain) and has no effect on SREPB-1c and the fatty acid synthase (FAS), thus indicating that FXR activation by the compounds of the invention allows selective modulation of genes involved in bile acid excretion with no effect on genes involved in lipid, cholesterol and glucose metabolism. Therefore, compounds of formula (I) act as a selective modulators of the bile acid transporters BSEP and increase the flux of biliary acids in the liver without inducing SHP; for this reason they can be used for the prevention or treatment of FXR-mediated diseases or conditions, which include liver diseases or conditions (involving one or more of cholestasis, steatosis, inflammation, fibrosis, and cirrhosis), gastrointestinal diseases or conditions, renal diseases or conditions, cardiovascular diseases or conditions, and metabolic diseases or conditions. Liver diseases or conditions which may be prevented or treated using compounds of formula (I) include but are not limited to primary biliary cirrhosis (PBC), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, viral hepatitis, alcoholic liver disease, nonalcoholic fatty liver disease (NAFLD), nonalcoholic steatohepatitis (NASH), graft versus host disease, transplant liver regeneration, congenital hepatic fibrosis, choledocholithiasis, granulomatous liver disease, intra- or extrahepatic malignancy, Sjogren's syndrome, sarcoidosis, Wilson's disease, Gaucher's disease, hemochromatosis, and α₁-antitrypsin deficiency. Gastrointestinal diseases or conditions which may be prevented or treated using compounds of formula (I) include but are not limited to inflammatory bowel disease (IBD) (including Crohn's disease and ulcerative colitis), irritable bowel syndrome (IBS), bacterial overgrowth, malabsorption, post-radiation colitis, and microscopic colitis. Renal diseases or conditions which may be prevented or treated using compounds of formula (I) include but are not limited to diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease. Cardiovascular diseases or conditions which may be prevented or treated using compounds of formula (I) include but are not limited to atherosclerosis, arteriosclerosis, dyslipidemia, hypercholesterolemia, and hypertriglyceridemia. Metabolic diseases or conditions which may be prevented or treated using compounds of formula (I) include but are not limited to insulin resistance, diabetes, and obesity.

The methods of the present invention comprise the step of administering a therapeutically effective amount of a compound of formula (I). As used herein, the term "therapeutically effective amount" refers to an amount of a compound of formula (I) which is sufficient to achieve the stated effect. Accordingly, a therapeutically effective amount of a compound of formula (I) used in a method for the prevention or treatment of FXR mediated diseases or conditions will be an amount sufficient to prevent or treat the FXR mediated disease or condition. Thus, for example, a therapeutically effective amount of a compound of formula (I) for use in a method for the prophylaxis or treatment of cholestatic liver diseases or increasing bile flow will be an amount sufficient to increase bile flow to the intestine.

The amount of a compound of formula (I) which is required to achieve the desired biological effect will depend on a number of factors such as the use for which it is intended, the means of administration, and the recipient, and will be ultimately at the discretion of the attendant physician or veterinarian. In general, a typical daily dose for the treatment of FXR mediated diseases and conditions, for instance, may be expected to lie in the range of from about 0.01 mg/kg to about 100 mg/kg. This dose may be administered as a single unit dose or as several separate unit doses or as a continuous infusion.

Thus, in a further aspect, the present invention provides pharmaceutical compositions comprising, as active ingredient, a compound of formula (I) together, and/or in admixture, with at least one pharmaceutical carrier or diluent. These pharmaceutical compositions may be used in the prophylaxis and treatment of the foregoing diseases or conditions.

The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired, other physiologically active ingredients may also be incorporated in the pharmaceutical compositions of the invention.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of FXR mediated diseases and conditions.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavoured base, such as sugar and acacia or tragacanth and pastilles comprising the active compound in an inert base, such as gelatine and glycerine or sucrose acacia.

Formulations suitable for parenteral administration typically comprise sterile aqueous solutions containing a predetermined concentration of the active compound; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Suitable formulations for administration by inhalation include fine particle dusts or mists which may be generated by means of various types of metered dose pressurised aerosols, nebulisers, or insufflators.

For pulmonary administration via the mouth, the particle size of the powder or droplets is typically in the range 0.5-10 μm, preferably 1-5 μm, to ensure delivery into the bronchial tree. For nasal administration, a particle size in the range 10-500 μm is preferred to ensure retention in the nasal cavity.

Metered dose inhalers are pressurised aerosol dispensers, typically containing a suspension or solution formulation of the active ingredient in a liquefied propellant. During use, these devices discharge the formulation through a valve adapted to deliver a metered volume, typically from 10 to 150 μl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavouring agents.

Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavouring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavouring agents and formulations suitable for intranasal administration may include perfumes.

Therefore, according to a further aspect of the present invention, there is provided the use of the compounds of formula (I) in the preparation of medicaments for the prevention or treatment of FXR mediated diseases or conditions.

The methods of the present invention are useful for the treatment of mammals generally and particularly humans.

The invention will be hereinafter illustrated in more detail in the following experimental section.

EXAMPLES

Chemistry

Melting points were determined with a Buchi 535 electrothermal apparatus and are not corrected. NMR spectra were obtained with a Bruker AC 200 MHz or 400 MHZ spectrometer and the chemical shifts are reported in parts per million (ppm). The abbreviations used are as follows: s, singlet; bs, broad singlet; d, doublet; dd, double doublet; m, multiplet. Specific rotations were recorded on a Jasco Dip-360 digital polarimeter. Flash column chromatography was performed using Merck silica gel 60 (0.040-0.063 mm). TLC were carried out on pre-coated TLC plates with silica gel 60 F-254 (Merck). Spots were visualized by staining and warming with phosphomolybdate reagent (5% solution in EtOH). All reactions were carried out under a nitrogen atmosphere.

Synthesis of 3α,7α-diformyloxy-5β-cholan-24-oic acid (V)

CDCA (II) (15.0 g, 38.27 mmol) was dissolved in 83 ml of tetrahydrofuran and treated with 18 drops of 70% $HClO_4$. Formic acid (50 ml) was then added dropwise in 40 min and the resulting mixture was reacted at 54° C. for 8 h. The mixture was then concentrated under vacuum and the residue was taken up in water. The white precipitate was filtered, washed several times with water, triturated in water at 5° C. for 20 min, and dried under high vacuum to obtain 16.5 g (36.83 mmol, 96%) of pure compound (V).

$^1$H-NMR (CDCl$_3$) δ: 0.54 (s, 3H, 18-CH$_3$), 0.80-0.84 (6H, 19-CH$_3$ and 21-CH$_3$), 2.24-2.57 (m, 2H, 23-CH$_2$), 4.52-4.76 (m, 1H, 3-CH), 4.91 (m, 1H, 7-CH), 7.92 (s, 1H, CHO), 7.97 (s, 1H, CHO).

Synthesis of Compound (VI)

3α,7α-Diformyloxy-5β-cholan-24-oic acid (V) (6.0 g, 13.37 mmol) was treated with oxalyl chloride (7.0 ml) and reacted at 35° C. for 3 h under nitrogen atmosphere. Removal of oxalyl chloride by evaporation gave the corresponding acid chloride, which was dissolved in dry acetone (50 ml). A solution of $NaN_3$ (5.2 g, 80.25 mmol) in water (25 ml) was added to the solution at 0-5° C. and the resulting reaction mixture was stirred for additional 3 h at the same temperature. The solvents were removed and the residue poured into cold water (100 ml) and extracted with diethyl ether (3×100 ml). The combined organic phases were dried over anhydrous $Na_2SO_4$ and evaporated to obtain the corresponding acylazide (IR: 2134 and 2267 $cm^{-1}$). The resulting acylazide intermediate was then refluxed in dry toluene (60 ml) for 5 h. The mixture was evaporated under vacuum to give 5.1 g of the isocyanate derivative 3 (11.37 mmol, 85%, IR: 2271 $cm^{-1}$) that was used for the next step without purification.

Synthesis of 23-N-Carbacinnamyloxy-3α,7α-dihydroxy-5β-norcholanylamine (Ia)

Isocyanate (VI) (5.0 g, 11.25 mmol) was dissolved in dry toluene (25 ml) and then reacted with cinnamyl alcohol (1.2 eq.) at 90° C. under nitrogen atmosphere. The end of the reaction was checked by TLC. The reaction mixture was then poured in water (50 ml), the organic phase was separated and the aqueous phase was extracted with ethyl acetate (3×25 ml). The combined organic phases were washed with brine, dried ($Na_2SO_4$), filtered and concentrated under vacuum. The crude 23-N-carboxy-3α,7α-diformyloxy-5β-norcholanylamine derivative were then treated overnight with a saturated methanol solution of $K_2CO_3$ (25 ml) at room temperature. After evaporation of the solvent, the residue was dissolved in water (35 ml), acidified with 2 N HCl and extracted with dichloromethane (3×25 ml). The combined organic extracts were dried over anhydrous $Na_2SO_4$, filtered, concentrated under vacuum and purified by silica gel flash chromatography using a mixture of dichloromethane/methanol as eluent, affording the desired compound (Ia) in good yields (72%).

mp: 79-84° C.

$^1$H-NMR ($CDCl_3$) δ: 0.67 (s, 3H, 18-$CH_3$), 0.92 (s, 3H, 19-$CH_3$), 0.98-0.99 (d, 3H, 21-$CH_3$), 3.09-3.22 (m, 1H, 23-$CH_2$), 3.23-3.31 (m, 1H, 23-$CH_2$); 3.46-3.57 (m, 1H, 3-CH), 3.86 (s, 1H, 7-CH), 4.73-4.74 (d, 2H, —$OCH_2CH$), 6.28-6.35 (m, 1H, —$OCH_2CH$), 6.63-6.68 (d, 1H, —CHPh), 7.25-7.41 (m, 5H, Ph). $^{13}$C-NMR ($CDCl_3$) δ: 11.64, 18.52, 20.46, 22.66, 23.58, 28.24, 30.50, 32.73, 33.67, 34.47, 34.94, 35.21, 36.08, 38.59, 39.30, 39.51, 39.70, 41.36, 42.62, 50.34, 55.91, 65.20, 68.41, 71.92, 123.96, 126.49, 127.83, 128.46, 133.47, 136.28, 153.43.

Biological Activity

Tests were first carried out in order to verify if compound (Ia) modulates FXR-regulated genes, in comparison with chenodeoxycholic acid (CDCA). CDCA is a primary bile acid that functions as endogenous ligand of the farnesoid-x-receptor (FXR; NR1H4). The biological activity of compound (Ia) on FXR activity was first tested in an vitro assay using the fluorescence resonance energy transfer (FRET) technology. This technology, a cell free assay, is described in Pellicciari R., et al. J Med Chem. 2002 15; 45:3569-72). In a cell-free assay, which uses FRE, the recruitment of Scr-1, a co-activating factor for FXR, occurs at a concentration of compound (Ia) that is almost 20-fold lower than that required for the natural FXR-ligand CDCA.

TABLE 1

Activity of compound (Ia) on Human FXR on FRET

| Compound Tested | Cell-Free Assay $EC_{50}$ (μM) | Efficacy[1] |
|---|---|---|
| Compound (Ia) | 0.592 | 66 |
| CDCA | 8.71 | 100 ± 3 |

[1]Relative recruitment of the SRC1 peptide to FXR where CDCA = 100%.
All data are mean ± SE, n = 4.

It was also evaluated if compound (Ia) modulated FXR-regulated genes in a cellular assay using a human hepatocyte cell line (HepG2). In a cell transfection assay using the HepG2 cell line, compound (Ia) proved a potent FXR ligand. Exposure of HepG2 cells to 1 μM of compound (Ia) transactivates FXR. In other experiments using liver cells transfected with viral constructs carrying the FXR gene or other nuclear receptors cloned upstream to the luciferase gene, it was found that compound (Ia) functions as a selective FXR ligand in mouse, rat, and human hepatocytes. A detailed description of these methods can be found in the following reference: Fiorucci S., et al. Gastroenterology 2004.

Regulation of FXR Target Gene Expression by Compound (Ia) in HepG2 Cells

To establish if compound (Ia) is a FXR modulator and exerts differential activities, human HepG2 cells were exposed to compound (Ia), CDCA (natural FXR ligand) and to its 6-ethyl-derivative, 6-ECDCA, which is a potent FXR ligand. The effects of these ligands on FXR responsive genes was then investigated by quantitative reverse transcription PCR (qRT-PCR). While no direct cell toxicity was observed upon exposure to any of these ligands, exposure of HepG2 cells to CDCA and its 6-ECDCA derivative, resulted in a 2-3 fold induction of SHP, an FXR regulated gene. By contrast, despite the fact that compound (Ia) is a FXR ligand (see above), it failed to stimulate SHP expression. All the FXR ligand tested, namely CDCA, 6-ECDCA and compound (Ia) exerted the same effect on CYP7α1 (all agents caused a 60-70% reduction of the expression of CYP7α1 mRNA). In addition, exposure to compound (Ia) resulted in a potent induction of BSEP mRNA expression (approximately 13 fold induction). This effect was significantly more pronounced with compound (Ia) than with the other FXR ligands. Furthermore, similarly to the other ligands, exposure to compound (Ia) resulted in a similar inhibitory activity on SREPB-1c and FAS mRNA expression. Taken together, these data suggest that compound (Ia) is an FXR modulator that functions as a potent FXR ligand, and unexpectedly alters FXR regulated genes, causing significant induction of bile acid transporters (for example BSEP), without inducing SHP. In addition, compound (Ia) represses the expression of Cyp7α1, a gene that is critically involved in bile acid synthesis from cholesterol. The regulation of these FXR target genes proves that compound (Ia) is a gene-selective FXR ligand that may inhibit bile acid biosynthesis through the classical pathway while increasing bile acid secretion from hepatocytes, without interfering with SHP expression. This effect is desirable, since it narrows the pharmacological activities of these FXR ligands, and might prevent metabolic activation typically associated with SHP induction.

The results of these experiments are resumed in Table 2 and are graphically represented in FIG. 1.

TABLE 2

| | | In Vitro Pharmacology Studies on compound (Ia) | | | |
|---|---|---|---|---|---|
| Cells | Test Article | Doses | Species | Endpoints | Summary Findings |
| Cell free assay | Compound (Ia) CDCA | Concentrations ranging from 1 nM to 100 μM | n/a | Potency of compound Ia as an FXR ligand in a cell free assay using FRET assay | The results of these experiments show that compound Ia is a potent ligand of FXR (EC$_{50}$ ~500 nM) |
| Hepatoma (HepG2) | Compound (Ia) CDCA 6-ECDCA | Concentrations ranging from 1 to 100 μM | Human | Potency on regulation of FXR and FXR regulated genes (SHP, CYP7α1, CYP8β1, SREPB1c, FAS and BSEP) | Compound (Ia) causes transactivation of FXR and is a potent inducer of BSEP with no effect on SHP. Compound (Ia) inhibits cyp7α1 expression. |

The invention claimed is:

1. A compound of formula (I)

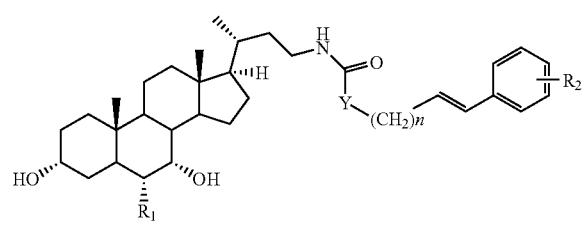

(I)

wherein:
$R_1$ is hydrogen or an alkyl group;
$R_2$ is hydrogen or a halogen, nitro, alkyloxy, amino or carboxy group;
Y is $CH_2$, oxygen or sulfur; and
n is an integer from 1 to 4, or a pharmaceutically acceptable salt thereof.

2. The compound of claim 1, wherein $R_1$ and $R_2$ are hydrogen, Y is oxygen, and n is 1.

3. A pharmaceutical composition containing a compound of claim 1 in admixture with pharmaceutically acceptable carriers and/or diluents.

4. A compound of formula (Ia)

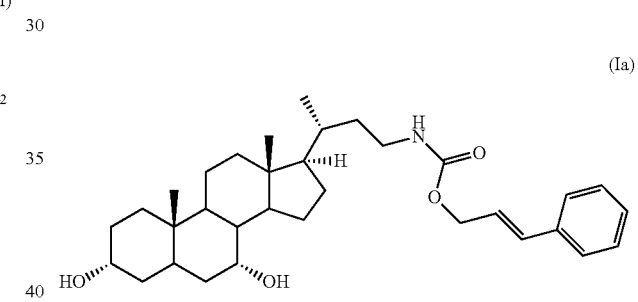

(Ia)

or a pharmaceutically acceptable salt thereof.

5. The pharmaceutical composition containing a compound of claim 4 in admixture with pharmaceutically acceptable carriers and/or diluents.

* * * * *